United States Patent
Schetky et al.

(10) Patent No.: US 6,419,358 B1
(45) Date of Patent: Jul. 16, 2002

(54) PSEUDOELASTIC β TITANIUM EYEGLASS COMPONENTS

(75) Inventors: L. McDonald Schetky, Camden, ME (US); Ming H. Wu, Bethel; Chi-Yuan Lei, Easton, both of CT (US)

(73) Assignee: Memry Corporation, Bethel, CT (US)

(*) Notice: Subject to any disclaimer, the term of this patent is extended or adjusted under 35 U.S.C. 154(b) by 0 days.

(21) Appl. No.: 09/449,068

(22) Filed: Nov. 24, 1999

Related U.S. Application Data

(63) Continuation-in-part of application No. 09/263,658, filed on Mar. 5, 1999, now Pat. No. 6,258,182.
(60) Provisional application No. 60/076,922, filed on Mar. 5, 1998.

(51) Int. Cl.[7] .................................................. G02C 5/16
(52) U.S. Cl. ......................... 351/114; 351/41; 351/126
(58) Field of Search .......................... 351/41, 111, 114, 351/124, 126

(56) References Cited

U.S. PATENT DOCUMENTS

| | | | |
|---|---|---|---|
| 4,895,438 A | * 1/1990 | Zider et al. ................ | 351/114 |
| 4,983,029 A | * 1/1991 | Sato ............................ | 351/41 |
| 5,409,015 A | * 4/1995 | Palermo ..................... | 128/772 |
| 6,077,368 A | 6/2000 | Nakamura et al. .......... | 148/563 |

* cited by examiner

Primary Examiner—Huy Mai
(74) Attorney, Agent, or Firm—Jerry Cohen; Harvey Kaye; Pekins, Smith, Cohen

(57) ABSTRACT

A new eyeglass frame, eyeglass frame component and method for making eyeglass frames or parts thereof of a nickel-free titanium based SMA. A pseudoelastic β titanium alloy is used which has superior fabricating characteristics combined with weldability with pseudoelastic properties over the temperature range of −25° C. to 50° C. making this alloy ideally suited for the manufacture of various eyeglass components. The disclosed eyeglass component alloy is a β titanium alloy contains alloying elements of molybdenum between 10.0 and 12.0 weight percent, aluminum between 2.8 and 4.0 weight percent, chromium and vanadium between 0.0 and 2.0 weight percent, and niobium between 0.0 and 4.0 weight percent. The eyeglass components fabricated from this alloy exhibit a strain recovery of up to 3.5% deformation, a lower stiffness than conventional binary nickel titanium alloys yielding superior wearer comfort.

21 Claims, 9 Drawing Sheets

□ 780 °C
♦ 830 °C
■ 880 °C

PSEUDOELASTIC β TITANIUM EYEGLASS COMPONENTS

CROSS REFERENCE TO REALTED APPLICATIONS

The present application is a continuation-in-part of a previously filed application, Ser. No. 09/263,658 filed Mar. 5, 1999, now U.S. Pat. No. 6,258,182, which obtains the benefit of a previously filed Provisional application Ser. No. 60/076,922 filed Mar. 5, 1998.

FIELD OF THE INVENTION

The present invention relates generally to the fabrication of eyeglasses, and, more particularly, to the making of eyeglass frames and parts thereof from a nickel-free titanium shape memory alloy.

BACKGROUND OF INVENTION

Eyeglasses

Alloys used in conventional eyeglass frames include stainless steel, copper based alloys and nickel-silver.

Shape Memory Effect and Pseudo-elasticity

The concept of using shape memory alloys for eyeglass components has been suggested in numerous articles and patents. Y. Suzuki, at that time head of shape memory alloy research at Furukawa Electric in Japan, published in Kinzoku Journal, vol. 31, No. 11, p115, 1981, the advantages of pseudoelastic shape memory alloy wire for fixing a lens into a frame. These findings were incorporated in one of the earliest patents on shape memory alloy applications for eyeglasses, Kokai Patent 56-89715, (Publication Date: Jul. 21, 1981) whose applications date back to 1979. Since these earlier studies, many other patents have issued claiming the advantages of using shape memory alloys for eyeglass components.

The driving force for making metal eyeglass frames from shape memory alloys lies in their great resistance to permanent deformation as compared to conventional alloys employed in this application.

Shape memory alloys belong to a class which exhibit what is termed thermoelastic martensite transformation. The term martensite refers to the crystalline phase which is produced in steels when quenched from a high temperature. The phase which exists at the elevated temperature is referred to as austenite; these terms have been carried over to describe the transformations which occur in shape memory alloys. When a steel has been quenched from the austenitic temperature to martensite, to again form austenite requires heating the structure to quite high temperatures, usually in excess of 1400° F. By contrast, the thermoelastic shape memory alloys can change from martensite to austenite and back again on heating and cooling over a very small temperature range, typically from 18 to 55° F. The transformation of a shape memory alloy is usually described by its hysteresis curve.

Materials which undergo martensite transformation may exhibit "Shape Memory Effect" and "Pseudo-elasticity." During the transformation on cooling, the high temperature phase known as "austenite" changes its crystalline structure through a diffusionless shear process adopting a less symmetrical structure called "martensite", and, on heating, the reverse transformation occurs. The starting temperature of the cooling transformation is referred to as the $M_s$ temperature and the finishing temperature, $M_f$. The starting and finishing temperatures of the reverse transformation on heating are referred to as $A_s$ and $A_f$ respectively.

Materials exhibiting Shape Memory Effect can be deformed in their martensitic phase and upon heating recover their original shapes. These materials can also be deformed in their austenitic phase above the $A_f$ temperature through stress-induced martensitic transformation and recover their original shapes upon unloading. This strain recovery, referred to as "pseudo-elasticity" [sometimes referred to herein as "PE"] is associated with the reversion of stress-induced martensite back to austenite. A well known shape memory alloy is nitinol, a near-stoichiometric alloy of nickel and titanium.

The Alloy Material

Pure titanium has an isomorphous transformation at 882° C. The body centered cubic (bcc) structure, so called β-Ti, is stable above the isomorphous point and the hexagonal close packed (hcp) structure, so called α-Ti, is stable below. When alloyed with elements such as vanadium, molybdenum, or niobium, the resulting alloys have an extended β phase stability below 882° C. On the contrary, when alloyed with elements such as Al or oxygen, the temperature range of stable α phase extends above the isomorphous point. Elements which have the effect of extending the β phase temperature range are called the β stabilizers while those capable of extending the α phase temperature range are called the α stabilizers.

For alloys with. a high enough concentration of β stabilizer elements, the material would be sufficiently stabilized to obtain a meta-stable β phase structure at room temperature. The alloys showing such a property are called β titanium alloys. Martensite transformations are commonly found among β titanium alloys. The $M_S$ temperatures in β-Ti alloys decrease with increasing amount of β stabilizer in the alloys, while increasing amount of α stabilizer raises the $M_S$. The dependence of $M_S$ on the concentration of some transition metals in binary titanium alloys is shown in FIG. 14 ['The Martensite Transformation Temperature in Titanium Binary Alloys', Paul Duwez, Trans. ASM, vol. 45, pp.934–940, 1953]. Therefore, depending on the extent of stabilization, β-Ti alloys may exhibit martensitic transformation when cooled very quickly from temperatures above the β transus, the temperatures above which β is the single phase at equilibrium.

To exhibit PE at room temperature, the alloys must be sufficiently β stabilized to have the $A_f$ point suppressed to below the ambient, but still allow the formation of stress-induced martensite before plastic deformation occurs. That is, the stress level for the martensite to form must be lower than that of plastic deformation. Shape memory effect, on the other hand, is observed when an alloy has an $A_s$ point higher than and $M_S$ temperature slightly below room temperature. Stress-induced martensite transformations have also been observed in β titanium alloys ['Formation and Reversion of Stress Induced Martensite in Ti—10V—2Fe—3Al', T.W. Duerig, J Albrecht, D. Richter and P. Fischer, Acta Metall., vol. 30, pp.2161–2172, 1982].

Both shape memory effect and pseudo-elasticity have been observed in certain Ti—Mo—Al β titanium alloys ['Shape Memory Effect in Ti—Mo—Al Alloys', Hisaoki Sasano and Toshiyuki Suzuki, Proc. 5th Int. Conf. on Titanium, Munich, Germany, pp.1667–1674, 1984]. In order to obtain SME or PE at room temperature the material has to be properly heat treated to produce the uniform β phase structure. The heat treatment to achieve that goal is called a solution treatment in which the test sample is heated to temperatures slightly above the β transus for a period of time long enough to allow for full austenization and then immediately cooled to room temperature.

Some β-Ti alloys, for example, TMA (Registered trade mark of Ormco, Glendora, Calif.), has been successfully commercialized for orthodontic arch wire application. The detailed description of the applications and properties of β titanium wires can be found in U.S. Pat. No. 4,197,643. The TMA wires show a unique balance of low stiffness, high spring-back, good formability ['Beta titanium: A new orthodontic alloy', C. Burstone and A. Jon Goldberg, American Journal of orthodontics, pp.121–132, February 1980], and weldability. ['Optimal welding of beta titanium orthodontic wires', Kenneth R. Nelson et al, American Journal of Orthodontics and Dentofacial Orthopedics, pp.213–219, September 1987]. The nickel-free chemistry of the alloy makes it more tolerable to some eyeglass wearers. However, TMA wires utilize the inherent mechanical properties of the material through thermo-mechanical processing. The material does not exhibit PE due to the occurrence and reversion of stress-induced martensite in the material.

Eyeglass frames fabricated from shape memory alloys are known to possess the advantages of wearer comfort and great resistance to accidental damage. The alloy traditionally used for this purpose is an equiatomic nickel-titanium alloy which exhibits pseudoelastic properties. These alloys are difficult to form, and require very exacting heat treatment to yield the properties required for eyeglass components; in addition they cannot be readily fusion welded.

SUMMARY OF THE PRESENT INVENTION

An object of the present invention is to provide a titanium nickel-free SME alloy which is particularly useful for eyeglass components with no allergenic properties typical of other nickel containing PE alloys.

Another object of the present invention is to provide an alloy having pseudo-elastic properties and which is useful for eyeglass components.

A further object of the present invention is to provide super-elastic eyeglass components made from formable, weldable nickel-free shape memory alloy.

Yet a further object of the present invention is to provide nickel-free shape memory or pseudo-elastic compositions with good formabilty for the fabrication of eyeglass components.

These and other objects of the present invention are accomplished by forming eyeglasses and eyeglass components with a nickel-free β titanium alloy characterized by exhibiting pseudo-elasticity at −25° C. to 50° C. or greater due to the formation and reversion of stress-induced martensite. Such an alloy exhibits SME at room temperature when the $A_s$ temperature is higher than room temperature. Furthermore, the alloy exhibits pseudo-elasticity with lower stiffness and force output magnitude, and better formability than Nitinol, the ability to be welded to other appliances, and good corrosion resistance.

It is capable of being cold worked to 20% without significantly reducing the pseudo-elastic performance, whereby it can be cold formed into various shapes at ambient temperature while retaining the high spring-back characteristics of the pseudo-elastic phenomenon, and it can be made so that it exhibits pseudo-elasticity over a wider temperature range than typical Nitinol alloys.

A nickel-free β titanium having super-elastic properties by being cold worked in its martensitic state, the alloy exhibiting complete elastic behavior at strains up to 4%, thereby permitting the designing of eyeglass components which are resistant to permanent deformation or kinking. The nickel-free β titanium alloy may be formed from:

(a) between 10.0 and 12.0 wt. % molybdenum;

(b) between 2.8 and 4.0 wt. % aluminum;

(c) chromium and vanadium between 0.0 and 2.0 wt. % chromium and vanadium; and (d) between 0.0 and 4.0 wt. % niobium; and (e) the balance titanium.

There may be a balanced amount of the alloying elements, and an effective amount of at least one selected from the group consisting of chromium, vanadium and niobium.

In one arrangement it may be formed of molybdenum of 10.2 wt. %, aluminum of 2.8 wt. %, vanadium of 1.8 wt. %, niobium of 3.7 wt. % and the balance of titanium and exhibit pseudo-elasticity between 25 and −25° C.

In another arrangement it may be formed of molybdenum of 11.1 wt. %, aluminum of 2.95 wt. %, vanadium of 1.9 wt. %, niobium of 4.0 wt. % and the balance of titanium and exhibit pseudo-elasticity between 50 and −25° C.

It is also a method for making a nickel-free β titanium alloy, comprising the steps of alloying together:

(a) between 10.0 and 12.0 wt. % molybdenum;

(b) between 2.8 and 4.0 wt. % aluminum;

(c) chromium and vanadium between 0.0 and 2.0 wt. % chromium and vanadium; and (d) between 0.0 and 4.0 wt. % niobium; and (e) the balance titanium.

In this method the alloy can be cold worked up to 20% without significantly reducing the pseudo-elastic performance, whereby the alloy is capable of being cold formed into various shapes at ambient temperature while retaining the high spring-back characteristics of the pseudo-elastic phenomenon.

DETAILED DESCRIPTION OF THE INVENTION

All of the sample alloys in the matrix discussed below were prepared by double vacuum arc melting technique. The ingots were hot rolled and flattened to sheets of 1.27 mm in thickness. Oxides on the sheets were removed by double-disc grinding and lapping. The test specimens were cut from sheets and sealed in evacuated quartz tubes back-filled with argon. The capsules were then heated to 880° C. for 30 minutes and quenched into a water bath at ambient temperature. Aging experiments were conducted at 200, 300 and 400° C. using a nitride/nitrade salt bath.

Permanent deformation and pseudo-elastic recovery strains were determined by bend tests. Specimens, 0.51× 1.02×51 mm in dimension, were cut from the sheets and then solution treated. After heat treatment, the specimens were bent against rods of different radii to form a "U" shape. The angles between the straight portions were measured afterwards and the strain recovery calculated to be:

$$e(rec)32\ e(180-a)/180;$$

where "a" is the unrecovered angle and "e" is the outer-fiber bending strain.

Tensile strain recovery was measured by tensile elongation to 4% strain followed by unloading to zero stress. Dogbone tensile specimens with a cross sectional dimension of 0.90 mm×2.0 mm were used and the strain was monitored using an extensometer. An environmental chamber with electrical heating and $CO_2$ cooling capabilities provides a range of test temperature from −30° C. to 180° C.

The bending moment/deflection characteristics of wires were determined by flexural tests at a university laboratory. Specimens 0.41×0.56 mm in cross section were used. A torque gauge apparatus was used to apply an angular deflection to the wires. The angular deflection of the specimens was measured with a protractor. The couple necessary to create the angular displacement was resisted by a force at the free end through an anvil placed against the specimens. A 5 mm span length was used for all the tests.

Figure 1:
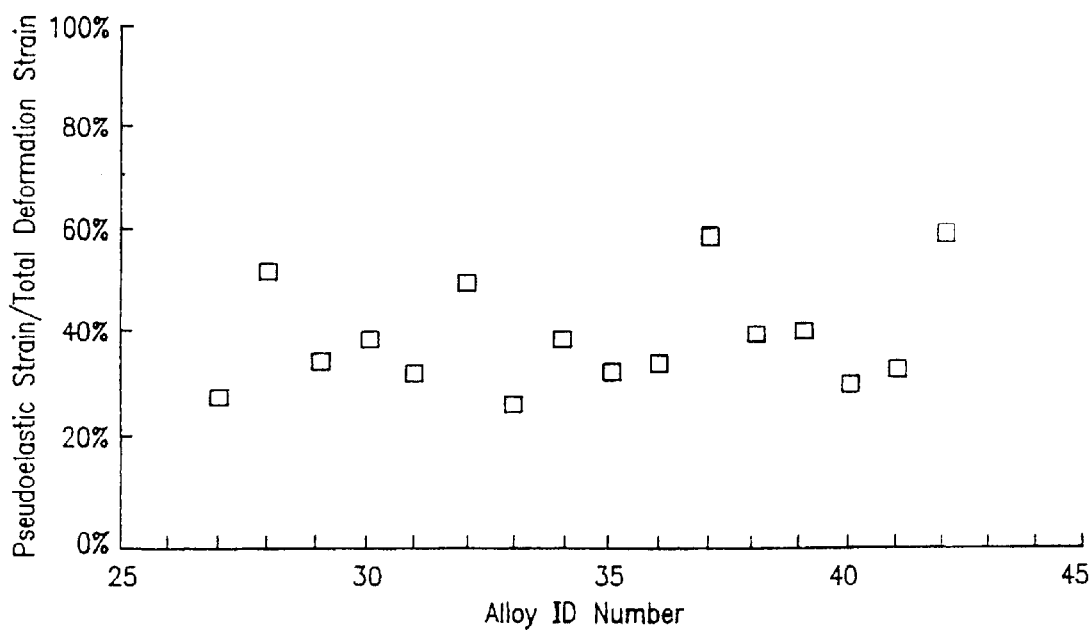
FIG. 1 is a graph showing the percentages of pseudo-elastic recovery strain relative to the bending strain for the fifteen alloys.

Bend tests at 6% bending strain were used for screening the alloys for their pseudo-elastic properties. The percentages of pseudo-elastic recovery strain relative to the bending strain for the fifteen alloys (one alloy was out-of-range and therefore was not used) are plotted in FIG. 1. Among the alloys, #42 exhibited the highest pseudo-elastic strain recovery and was selected for further studies.

Figure 2:
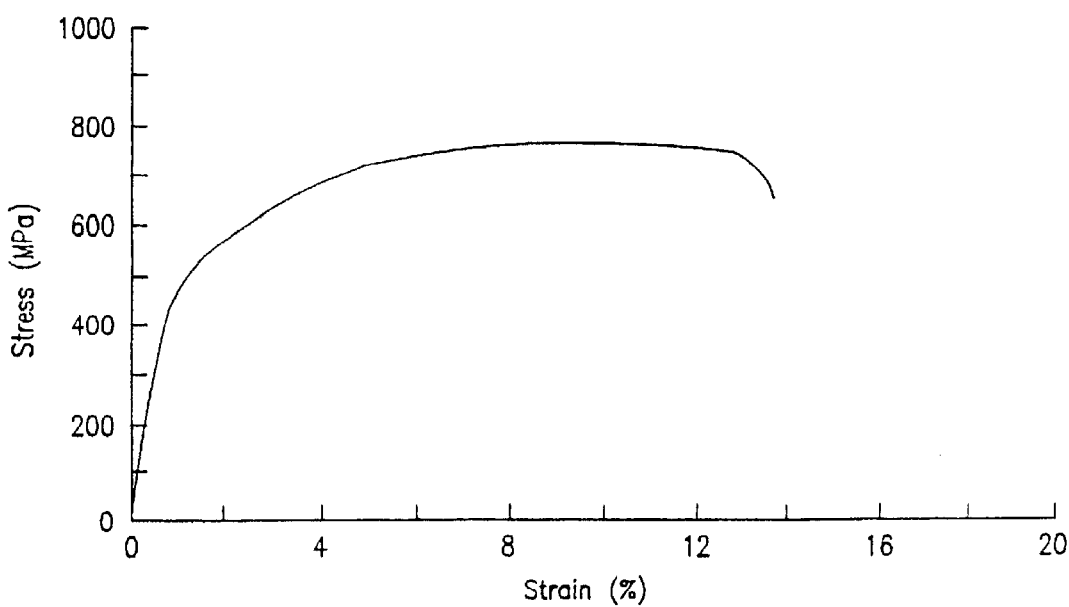
FIG. 2 is a graph showing a tensile stress-strain curve for alloy #42 tested to failure.
Figure 3A:
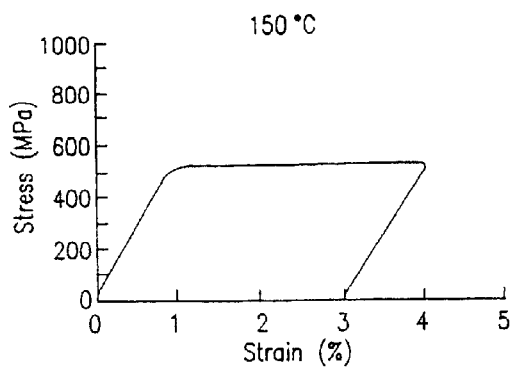
FIGS. 3(A–F) is a graph showing stress-strain curves of tensile loading to 4% strain followed by unloading to zero stress of alloy #42 tested at different temperatures.
Figure 3D:
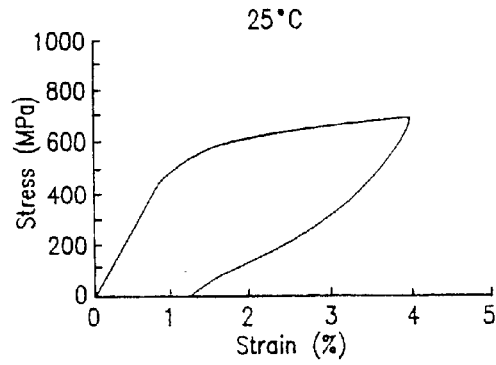
Figure 3B:
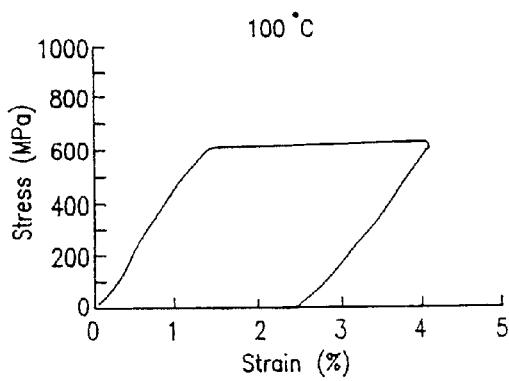
Figure 3E:
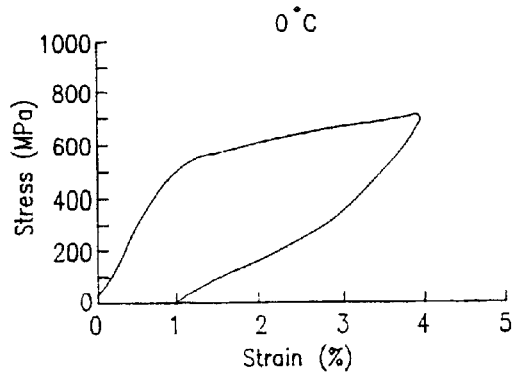
Figure 3C:
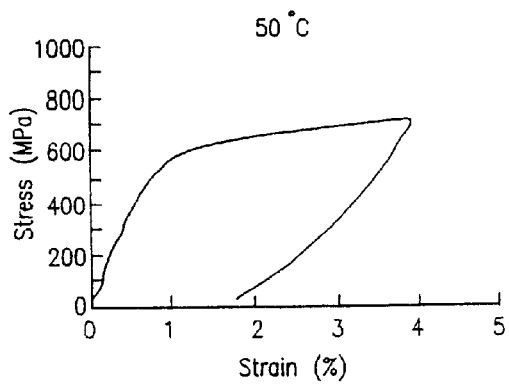
Figure 3F:
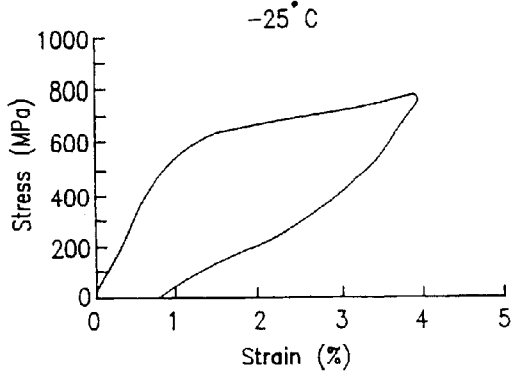

FIG. 2 shows a tensile stress-strain curve of alloy #42 tested to failure. The mechanical properties based on the curve are summarized in Table I. In absence of significant work hardening, the reduction in cross-section area (R.A.) is much higher than the tensile elongation and is a better indication of the true ductility of the alloy.

TABLE I

Mechanical properties of alloy #42.

| UTS | Yield Stress | Young's Modulus | R.A. | Tensile Elongation |
|---|---|---|---|---|
| 765 MPa | 500 MPa | 65 GPa | 27% | 13.7% |

Tensile loading/unloading hysteresis curves for alloy #42 tested to 4% strain at temperatures from −25° C. to 150° C. and are shown in FIG. 3.

A matrix of fifteen β titanium alloys with the composition range (wt. %) listed in Table II. were examined.

TABLE II

|  | Mo | Al | Cr | V | Nb |
|---|---|---|---|---|---|
| Low | 9.5 | 2 | 0 | 0 | 0 |
| High | 12 | 4 | 2 | 2 | 4 |

The alloys use molybdenum as the major β stabilizer and aluminum as the major α stabilizer. Their chemical compositions are listed in Table III. All specimens were subjected to a standard solution treatment of 10 minutes at 800° C. followed by quenching into a water bath at room temperature. Bend test results of as-solution treated specimens in Table III. show the alloys which exhibit SME or PE at room temperature. Out of the fifteen alloys screened, alloys #28, 32, 37, and 42 exhibited significant pseudo-elastic strain recovery, while alloys #31, 33 and 41 exhibited SME.

TABLE III

| Alloy ID | Mo | Al | Cr | V | Nb | ES (%) | SME (%) | PD (%) |
|---|---|---|---|---|---|---|---|---|
| 27 | 9.5 | 3.1 | 1.4 | 1.4 | 3.1 | 1.6 | 0 | 4.3 |
| 28 | 10.0 | 3.5 | 1.7 | 0 | 0 | 3 | 0 | 2.9 |
| 29 | 9.0 | 2.3 | 1.4 | 0 | 3.0 | 2 | 0.1 | 4 |
| 30 | 10.3 | 2.7 | 1.8 | 1.6 | 0 | 2.3 | 0.1 | 3.7 |
| 31 | 11.8 | 3.7 | 0 | 0 | 0 | 1.9 | 3.5 | 0.7 |
| 32 | 11.0 | 2.8 | 0 | 1.8 | 3.6 | 3.1 | 0.1 | 3.1 |
| 33 | 10.4 | 3.6 | 0 | 1.8 | 3.7 | 1.7 | 3.8 | 0.9 |
| 34 | 10.2 | 2.7 | 0 | 0 | 0 | 2.1 | 0 | 3.4 |
| 35 | 11.5 | 3.7 | 1.8 | 0 | 0 | 1.8 | 0 | 3.8 |
| 36 | 8.4 | 3.0 | 1.4 | 1.4 | 3.0 | 2 | 0.1 | 4 |
| 37 | 11.6 | 2.8 | 1.8 | 1.8 | 0 | 3.4 | 0 | 2.5 |
| 38 | 10.4 | 2.6 | 1.8 | 1.8 | 3.7 | 2.3 | 0.1 | 3.5 |
| 39 | 11.6 | 3.6 | 0 | 1.8 | 3.8 | 2.6 | 0.1 | 3.7 |
| 41 | 11.5 | 2.8 | 0 | 0 | 0 | 1.8 | 3.5 | 0.5 |
| 42 | 10.2 | 2.8 | 0 | 1.8 | 3.7 | 3.7 | 0.5 | 2.2 |

Figure 4:
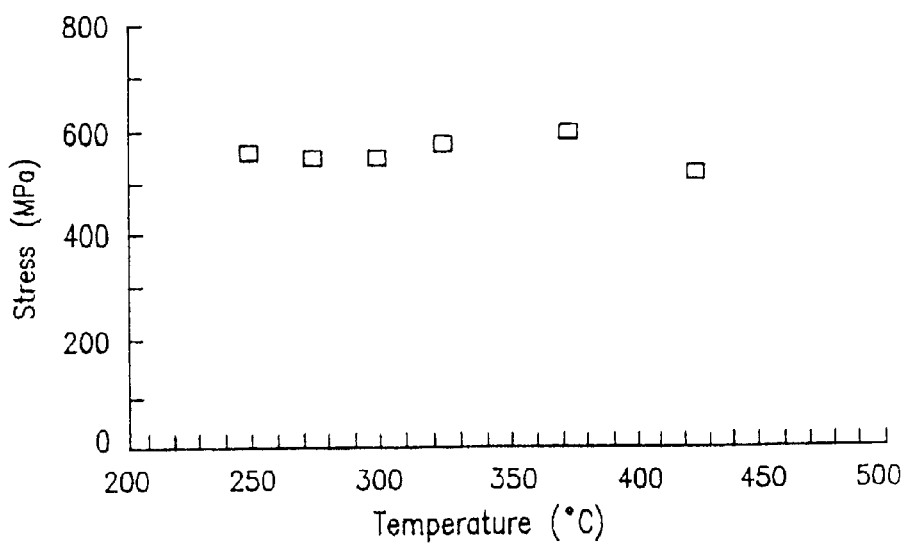
FIG. 4 is a plot showing the effect of temperature on the first yield of alloy #42.

ES - elastic spring-back
SME - shape memory strain recovery on heating
PD - permanent plastic deformation The tensile loading-unloading test gives accurate quantitative results on recovery and modulus, and therefore is a widely accepted way of characterizing materials exhibiting SME and PE. Stress-strain curves of tensile loading to 4% strain followed by unloading to zero stress tests on alloy #42 are in FIG. 3. Distinctive PE was observed in the temperature range between −25 and 25° C. Effects of cold work on the PE of alloy #42 were also studied by bend tests. The bend test results indicate that cold work up to 20% of as-solution treated specimens does not affect the strain recovery significantly (FIG. 3) where temperatures range from −25° C. to 150° C. well defined pseudo-elasticity was observed at temperatures below 25° C. The residual plastic deformation decreases as pseudo-elasticity becomes more pronounced with decreasing temperatures. The yield stress (critical stress to induce martensite) is relatively insensitive to the temperature as it decreases only slightly with decreasing temperature (FIG. 4).

Figure 5:
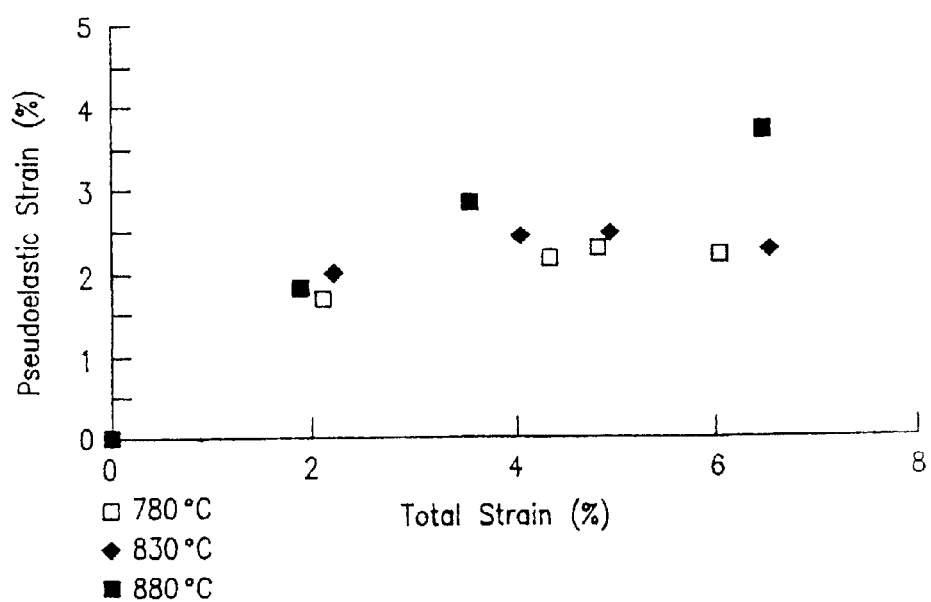
FIG. 5 is a plot of bend test results of alloy #42 showing the effect of solution treatment temperature on the strain recovery by bending.

The bend test results of #42 after solution-treatment at 880° C., 830° C. and 780° C. for 30 minutes are shown in FIG. 5. Specimens heat treated at temperatures lower than 880° C. resulted in lower amount of pseudo-elastic strain recovery.

Figure 6:
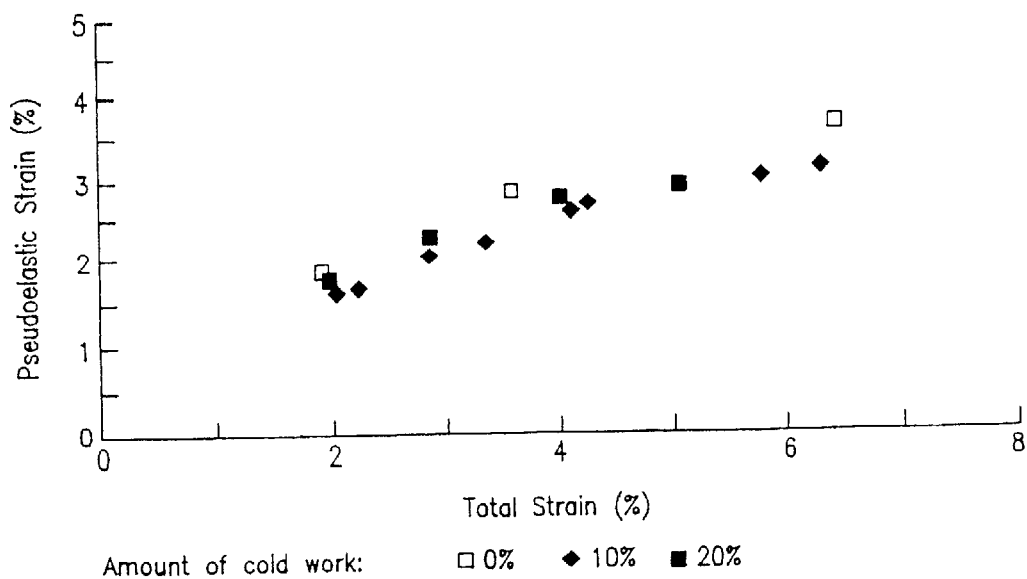
FIG. 6 is a plot of the pseudo-elastic recovery strain during bend tests of the cold-rolled samples.

Solution-treated sheets of alloy #42 were cold rolled to thickness with 10% and 20% reduction. The pseudo-elastic recovery strain during bend tests of the cold-rolled samples are plotted in FIG. 6. It can be seen that pseudo-elastic strain recovery decreases only slightly as a result of increasing amount of cold work, indicating that pseudo-elasticity in this alloy is not significantly affected by cold deformation up to 20%.

Figure 7:
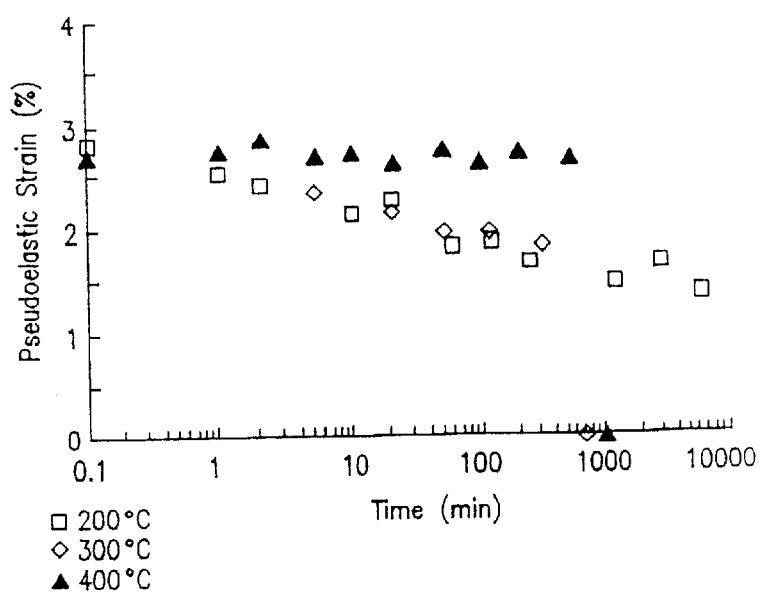
FIG. 7 is a plot of pseudo-elastic recovery strains of specimens after aging at 200, 300 and 400° C. against aging time.

Effects of aging at temperatures from 200 to 400° C. were studied by bend tests to 4% total outer-fiber bending strains. Pseudo-elastic recovery strains of specimens after aging at 200, 300 and 400° C. are plotted against aging time in FIG. 7. The pseudo-elastic recovery strain decreases from the as-solution-treated level of 2.8% to approximately 1.5% after one day of aging at 200° C. and to about 1.8% after five hours of aging at 300° C. It was also noted that ductility of the alloy decreases significantly during aging at these temperatures. The reductions in area measured after tensile test specimens with selected aging condition are listed in Table IV. Bend test specimens after aging at 300° C. for 600 minutes and 400° C. for 1000 minutes broke at 4% bending strain during the tests.

TABLE IV

Area (R.A.) of alloy #42 after aging treatment.

| Aging Treatment | R.A. |
|---|---|
| 200° C./50 hrs. | 12.6% |
| 300° C./60 min. | 14.1% |
| 300° C./100 min. | 9.5% |

The aging embrittlement at these low temperature is most likely related to the formation of ω-phase as two of the effects of ω-phase observed by Duerig et al, i.e., low work hardening and low ductility, are also observed in the specimens aged at 200 and 300° C.

Figure 9:
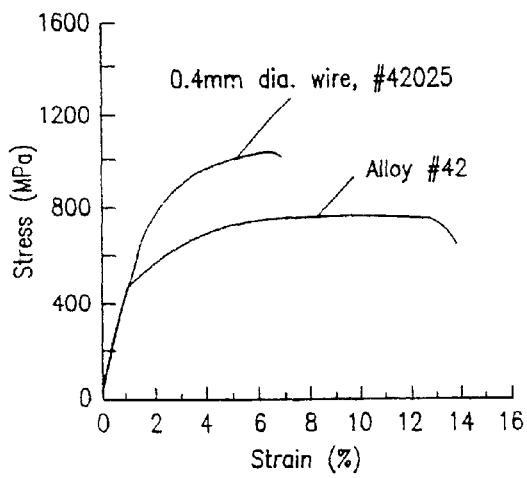
FIG. 9 tensile stress-strain curves of alloy #42025 and dogbone specimen of alloy #42.

The tensile stress-strain curves of alloy #42 as well as 0.4 mm diameter wire of alloy #42025 tested to failure are shown in FIG. 9. The tensile elongation of the #42025 specimen in the as-solution-treated condition is approximately 7 percent which is approximately half of what was obtained from #42 specimen. The ultimate tensile strength of the wire specimen is about 1000 MPa, significantly higher than that of #42, which is around 780 MPa. The mechanical properties based on the test data are summarized in Table I. In the absence of significant work hardening, the reduction in cross-section area (R.A.) is much higher than the tensile elongation and is a better indication of the true ductility of the alloy.

Figure 10:
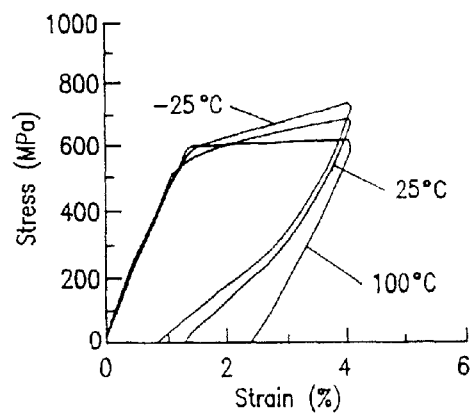
FIG. 10 tensile hysteresis curves of alloy #42 at three different temperatures.
Figure 11:
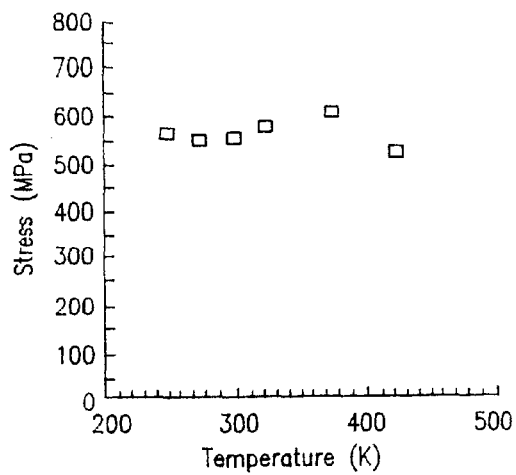
FIG. 11 yield stress of alloy #42 at different temperatures.

Tensile hysteresis curves tested to 4% strain at temperatures at −25, 25 and 100° C. are shown in FIG. 10. Well defined pseudo-elasticity was observed at temperatures below 25° C. The yield stress (critical stress to induce martensite) is relatively insensitive to the temperature as it decreases only slightly with decreasing temperature (FIG. 11). This indicates that the $A_f$ point of this alloy is below room temperature and $M_d$, the temperature above which PE cannot take place, is close to 100° C.

Figure 12:
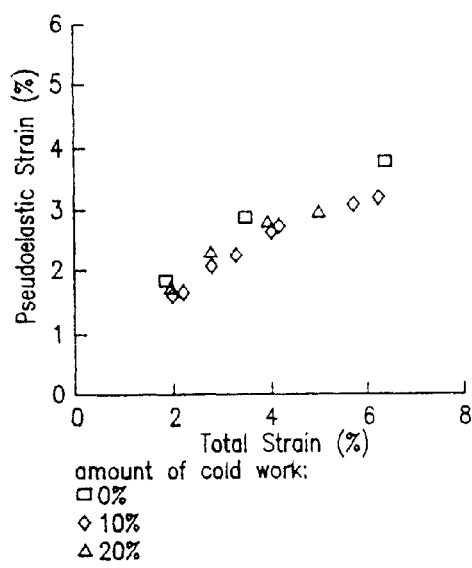
FIG. 12 effect of cold work on the pseudo-elastic strain of alloy #42.

Solution-treated sheets of alloy #42 were cold rolled to thickness with 10% and 20% reduction. The pseudo-elastic recovery strain by bend tests of samples with and without cold work are plotted in FIG. 12. It can be seen that pseudo-elastic strain recovery decreases only slightly as a result of increasing amount of cold work, indicating that pseudo-elasticity in this alloy is not significantly affected by cold deformation up to 20%.

The new alloy, X42025, based on the composition of alloy #42 was melted and processed to wires of 0.061" and 0.016" diameter. The wet chemical analysis showed that the alloy has a chemical composition of: Ti-11.14 wt. % Mo-2.95 wt. % Al-1.88 wt. % V-3.99 wt. % Nb. The tensile loading to 4% strain followed by unloading to zero stress curves of alloy X42025 are shown in FIG. 15. Again, the alloy exhibits distinct PE between −25° C. and 50° C.

Comparing the chemical compositions of alloys #42 and X42025, it is noted that even though the composition of molybdenum in X42025 is almost one percent higher than that of alloy #42, both exhibit significant PE in a quite similar temperature range. Since the martensite transformation temperatures are very sensitive to the molybdenum content, it is clear that a wide $A_f$ range exists for the alloys to exhibit PE at room temperature. By examining the chemical compositions of alloys with PE or SME, it is recognized that alloys with chemical compositions within the boundaries of: molybdenum between 10.0 and 12.0 wt. %, aluminum between 2.8 and 4.0 wt. %, chromium and vanadium between 0.0 and 2.0 wt. %, and niobium between 0.0 and 4.0 wt. %, would exhibit PE or SME when the transformation temperatures, decided by the proper balance of α and β stabilizers, fall in the right temperature range. With the experimental data available one skilled in the art can define the transformation temperature or operating temperature range required for either SME or PE.

Solution-treated sheets of alloy #42 were cold rolled to thickness with 10% and 20% reduction. The pseudo-elastic recovery strain by bend tests of samples with and without cold work are plotted in FIG. 12. It can be seen that pseudo-elastic strain recovery decreases only slightly as a result of increasing amount of cold work, indication that pseudo-elasticity in this alloy is not significantly affected by cold deformation up to 20%.

A good way to compare the mechanical performance between pseudo-elastic β titanium and other commercial shape memory wire materials is by the flexural test. Flexural tests produce the bending moment—activation angle curves which allow us to compare the relative force output, stiffness and spring-back among different wire materials. Flexural tests provide a direct comparison of bending moment—activation angle relationship among a variety of potential eyeglass wire materials, which is an important quantitative evaluation of a new alloy for this application. The flexural test curves of 18-8 stainless steel, Nitinol, TMA and alloy #42 of FIG. 8 indicates that alloy #42 has a combination of desirable characteristics. Alloy #42 has a spring-back characteristic comparable to that of TMA, which is between those of stainless steel and Nitinol. The force output, on the other hand, is similar to that of Nitinol. The data suggested that alloy #42 has the desirable combination of the following properties, a similar spring-back characteristics together with a lower stiffness when compared to those of TMA and better formability than that of Nitinol, and, in addition, based on experiments with similar β- titanium alloys exhibits good weldability.

Figure 8:
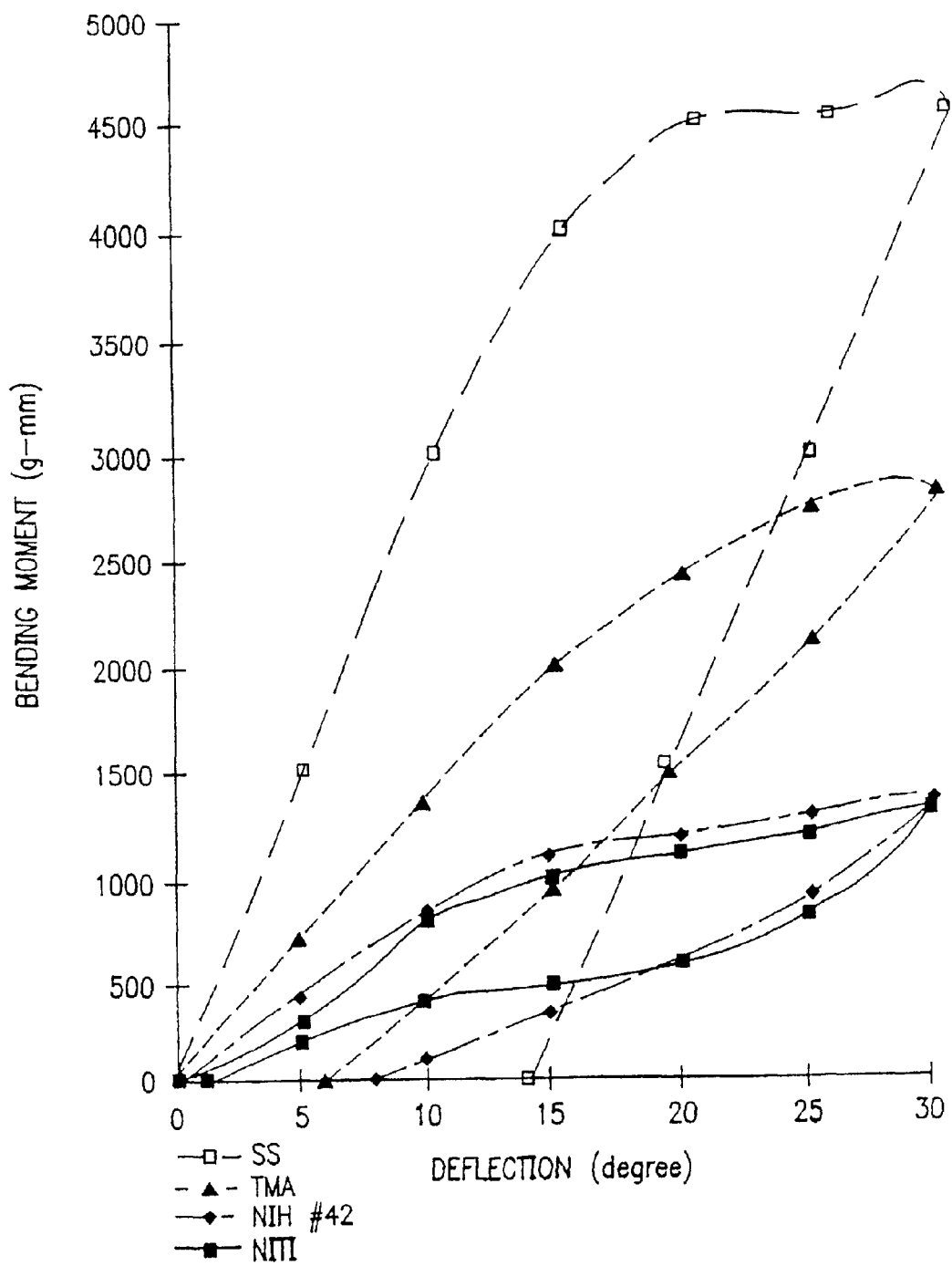
FIG. 8 is a comparison of the flexural test data of stainless steel, TMA, Nitinol and present alloy #42.

A detailed description of the test setup and method can be found in previous literature. ['Chinese NiTi wire-A new orthodontic alloy', by Charles J. Burstone et al, American Journal of Orthodontics, pp. 445–452, June, 1985] Flexural test curves of 18-8 stainless steel, Nitinol, TMA and alloy #42 are depicted in FIG. 8. The flexural test data indicates that alloy #42 has a combination of the following properties; a similar spring-back characteristics together with a lower stiffness when compared to those of TMA and better formability than that of Nitinol.

Figure 13:
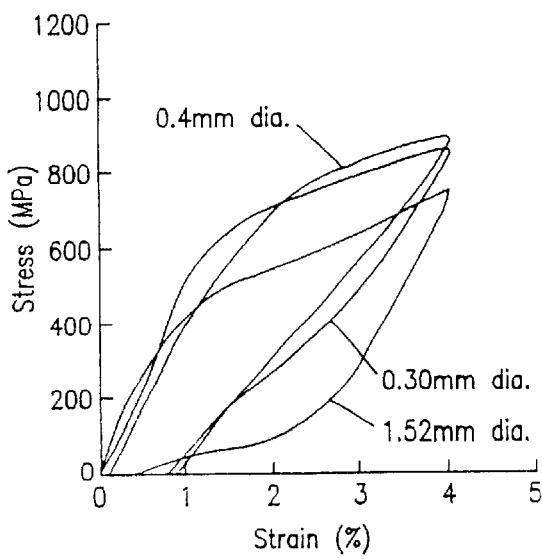
FIG. 13 is a graph of the 15 tensile hysteresis curves of as-solution treated wires of alloy #42025.
Figure 14:
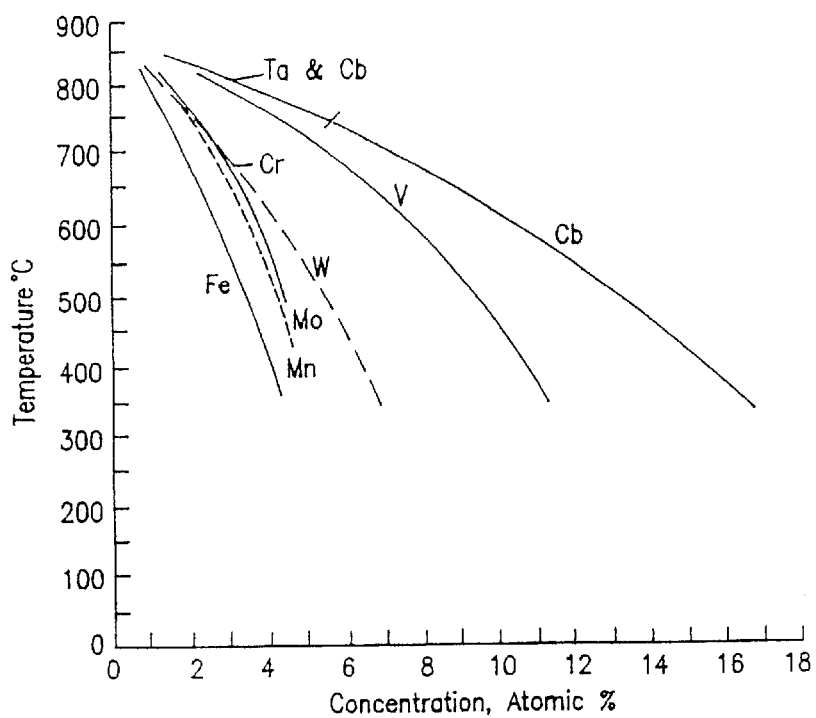
FIG. 14 is a graph showing the dependence of $M_s$ on the concentration of some transition metals in binary titanium alloys.
Figure 15A:
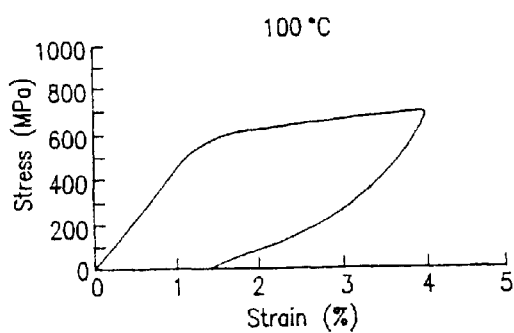
FIGS. 15 (A–E) is a graph showing the stress-strain curves of tensile loading to 4% strain followed by unloading to zero stress of alloy X42025 tested at different temperatures.
Figure 15D:
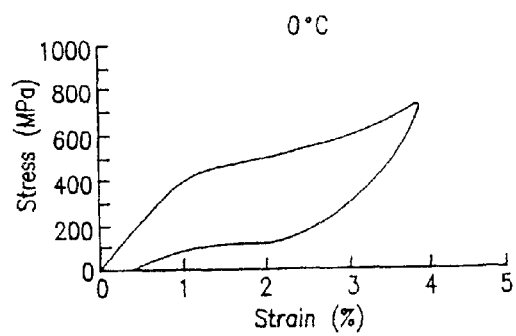
Figure 15B:
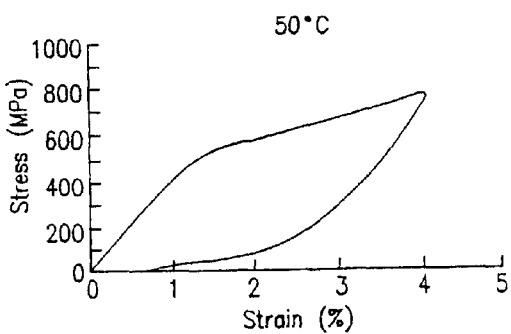
Figure 15E:
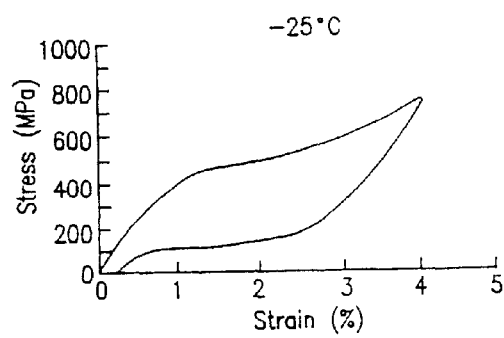
Figure 15C:
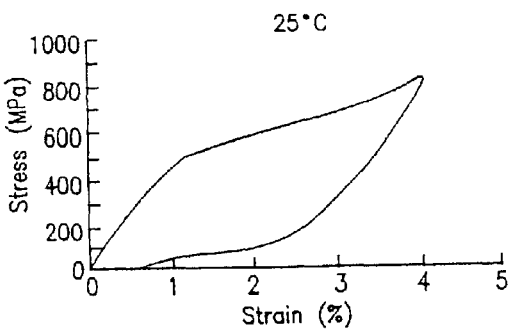

Part of the #42025 forged bar was cold drawn with inter-pass vacuum annealing down to wires of 1.52 mm and 0.40 mm in diameter with approximately 30% retained cold reduction in cross-section area. The pilot size trial for the production of alloy #42025 demonstrated that the alloy can be successfully processed to the desired size for orthodontic applications. The room temperature tensile hysteresis curves of 0.40 mm and 1.52 mm diameter wires in the as-quenched condition are shown in FIG. 13. Distinct pseudo-elasticity can be seen on the curve of 1.52 mm wire but almost nonexistent on the 0.40 mm wire curve.

A layer of contaminated structure was observed on the surface of the 0.40 mm wire but not on 1.52 mm wire sample. The surface layer of a piece of 0.40 wire was mechanically polished to approximately 0.30 mm diameter followed by solution treatment in argon. The resulting tensile hysteresis curve showed some improvement in pseudo-elasticity (FIG. 13).

The surface layer is believed to be α phase caused by oxygen infiltration during hot processing in air and is detrimental to the pseudo-elasticity of the alloy. Therefore, the production process needs to avoid extended high temperature exposure in any oxygen-containing atmosphere, especially in the latter stage of wire drawing to obtain materials with high pseudo-elastic springback for the eyeglass component applications.

Comparing the tensile hysteresis curves of #42 and 1.52 mm diameter wire of #42025, it is believed that, with optimized composition as well as a proper production and heat treating process, this material significantly improves its pseudo-elastic properties making it a more versatile and competitive material in eyeglass component fabrication applications. Alloy #42 as well as alloys of its class has a unique place in eyeglass usage. It is highly formable without adverse effect on pseudo-elasticity which allows the fabrication of ear pieces, nose wires and pad wires with variable cross section and varying levels of cold work.

Figure 16:
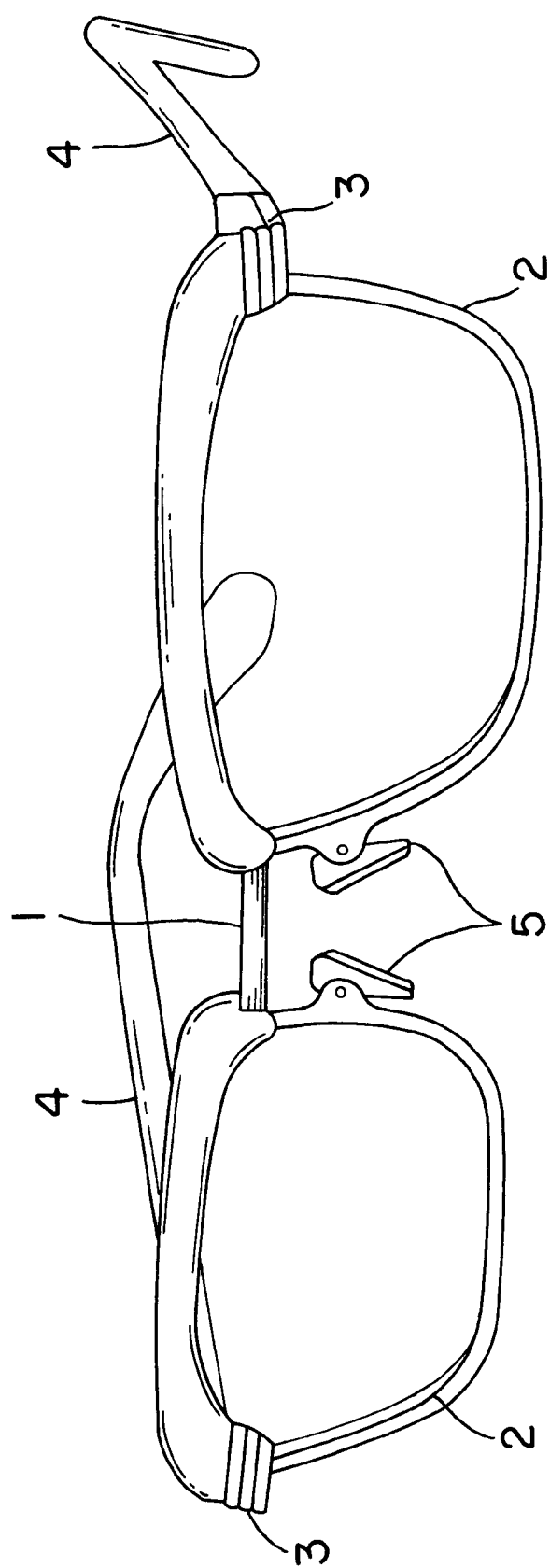
FIG. 16 is an isometric view of a eyeglass frame showing the various parts thereof.

FIG. 16 shows an eyeglass frame, part(s) or all of which may be made of the material provided by the present invention. The eyeglass frame includes the lens frames 2, the bridge 1, the hinges 3, the ear pieces 4 and the nose pieces 5.

Thus, a pseudo-elastic titanium alloy based on Ti—Mo—Al has been developed. The alloy, when properly solution treated, exhibits a well-defined pseudo-elastic behavior which is insensitive to decreasing temperature below the ambient. The pseudo-elastic behavior of the alloy is not significantly affected by cold work up to 20% reduction. Aging of the present alloy at temperatures in the range of 200 to 400° C. results in a decrease of pseudo-elastic strain recovery and loss in ductility. The alloy possesses desirable properties of good spring-back, low stiffness, and good formability for eyeglass application. When compared with other commercial eyeglass lens wires, and other eyeglass components, the present alloy exhibits spring-back similar to that of TMA and stiffness similar to that of nitinol, while being nickel-free.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

We claim:

1. In an eyeglass frame having at least one component thereof being fabricated of a shape memory effect alloy, the improvement comprising said component including at least one of a pair of temples, a bridge, a pair of lens rims and nose pads wires, said component being made of a β titanium alloy which comprises:
   (a) between 10.0 and 12.0 wt.% molybdenum;
   (b) between 2.8 and 4.0 wt.% aluminum;
   (c) chromium and vanadium each between 0.0 and 2.0 wt.% chromium; and
   (d) between 0.0 and 4.0 wt.% niobium; and
   (e) the balance titanium,
and characterised by exhibiting pseudo-elasticity at −25° C. to 50° C.

2. The improvement as defined in claim 1 wherein said component includes a pair of temples and a bridge.

3. The improvement as defined in claim 1 wherein said component includes a pair of lens rims.

4. The improvement as defined in claim 1 wherein said component includes a pair of lens rims, and a pair of nose pads wires, each nose pad being connected to a respective rim by a nose pad wire.

5. The improvement as defined in claim 1 in which the component exhibits shape memory effect at room temperature when the $A_s$ starting temperature of reverse transformation upon heating is higher than room temperature.

6. The improvement as defined in claim 1 in which the component exhibits pseudo-elasticity with lower stiffness and force output magnitude than conventional β titanium alloys, better formability than Nitinol, the ability to be welded to other components, and good corrosion resistance.

7. The improvement defined in claim 6, in which the component has a strain recovery up to approximately 3.5% when tensile loaded to 4% strain at room temperature in the as-solution treated condition.

8. The improvement as defined in claim 1 in which the component is capable of being cold worked to 20% without significantly reducing the pseudo-elastic performance, whereby said component can be cold formed into various shapes at ambient temperature while retaining the high spring-back characteristics of the pseudo-elastic phenomenon.

9. The improvement defined in claim 1 in which the component exhibits pseudo-elasticity between 25 and −25° C.

10. The improvement defined in claim 1 in which the component exhibits pseudo-elasticity at ambient and/or body temperature of a wearer.

11. The improvement defined in claim 1 in which the component is characterized by having super-elastic properties and by being cold worked in its martensitic state, said alloy exhibiting complete elastic behaviour at strains up to 4%, thereby permitting the designing of eyeglasses components which are resistant to permanent deformation or kinking.

12. The improvement defined in claim 1, wherein there is a balanced amount of the alloying elements, and an effective amount of at least one selected from the group consisting of chromium, vanadium and niobium.

13. The improvement defined in claim 1, wherein the alloy comprises, molybdenum of 10.2 wt.%, aluminum of 2.8 wt.%, vanadium of 1.8 w%, niobium of 3.7 wt.% and the balance of titanium and exhibiting pseudo-elasticity between 25 and −25° C.

14. The improvement defined in claim 1, wherein the alloy comprises molybdenum of 11.1 wt.%, aluminum of 2.95 wt.%, vanadium of 1.9 wt.%, niobium of 4.0 wt.% and the balance of titanium and exhibiting pseudo-elasticity between 50 and −25° C.

15. An eyeglass frame in which at least one of the components is constructed according to claim 1 wherein said component is made from a β-Titanium shape memory alloy, which in its solution treated condition is capable of undergoing large amounts of cold forming without danger of cracking or fracture during the forming operations required to make eyeglass frame components, and as a result facilitates the fabrication of such component.

16. An eyeglass frame in which at least one of the components is constructed according to claim 15 wherein the solution treatment of the alloy has been given at a temperature between 880° C. and 1100° C. and then water quenched.

17. An eyeglass frame in which at least one of the components is constructed according to claim 1, wherein relatively small amounts of cold work before the aging treatment do not exceed 20%.

18. An eyeglass frame in which at least one of the components is constructed according to claim 1 wherein the component exhibits pseudoelastic properties with an upper plateau stress which is between approximately 58 Ksi and 72 Ksi, which is a stress level comfortable to a wearer.

19. An eyeglass frame in which at least one of the components is constructed according to claim 1 wherein shape memory alloy, during fabrication, is subjected to a variety of cold working levels to create various cross sections of the portion, which nevertheless exhibit substantially uniform pseudoelastic properties.

20. The improvement as defined in claim 1 wherein said alloy is substantially free of nickel.

21. In a method for making at least one component of an eyeglass frame, the improvement comprising the steps of:
 a. forming β titanium alloy by alloying together:
  (i) between about 10.0 and 12.0 wt.% molybdenum;
  (ii) between about 2.8 and 4.0 wt.% aluminum;
  (iii) between about 0.0 and 2.0 wt.% chromium and vanadium;
  (iv) between about 0.0 and 4.0 wt.% niobium; and
  (v) the balance titanium;
 b. fabricating said at least one eyeglass frame componenet from said alloy, and said component including at least one of a pair of temples, a bridge, a pair of lens rims and nose pads wires.

* * * * *